United States Patent [19]

Hunsucker

[11] 4,066,433

[45] Jan. 3, 1978

[54] METHOD OF CONTROLLING THE GROWTH OF BACTERIA, FUNGI AND ALGAE USING MEMBERS OF THE CLASS OF OXAZOLIDINES

[75] Inventor: Jerry H. Hunsucker, Terre Haute, Ind.

[73] Assignee: IMC Chemical Group, Inc., Terre Haute, Ind.

[21] Appl. No.: 588,744

[22] Filed: June 20, 1975

Related U.S. Application Data

[62] Division of Ser. No. 469,200, May 13, 1974.

[51] Int. Cl.$^2$ .......................... A01N 9/00; A01N 9/22; A01N 9/28
[52] U.S. Cl. ................................. 71/67; 260/307 FA; 424/272
[58] Field of Search ............... 424/272; 260/307 FA; 71/67

[56] References Cited

U.S. PATENT DOCUMENTS

| 2,250,408 | 7/1941 | Groote | 260/307 FA X |
| 3,160,634 | 12/1964 | Hodge | 260/307 X |
| 3,256,137 | 6/1966 | Danielson | 260/307 FA X |
| 3,257,320 | 6/1966 | Hodge | 252/51.5 |
| 3,266,970 | 8/1966 | Paul | 161/241 |
| 3,281,311 | 10/1966 | Paul | 161/241 |
| 3,707,541 | 12/1972 | Lajiness | 260/244 R |
| 3,738,992 | 6/1973 | Frump | 260/307 F |
| 3,824,309 | 7/1974 | Schnegelberger | 424/272 |

FOREIGN PATENT DOCUMENTS 1,903,864 8/1970 Germany.

OTHER PUBLICATIONS

Senkus, J. Am. Chem. Soc., 67, 1515–1519, (1945).
Danielson, Chem. Abst. vol. 58, (1963) 12750b.

*Primary Examiner*—Allen J. Robinson
*Attorney, Agent, or Firm*—Robert H. Dewey; Howard E. Post

[57] ABSTRACT

A method of controlling the growth of bacteria, fungi, algae and viruses by applying to them, growth-inhibiting amounts of a monocyclic oxazolidine represented by a disclosed formula.

6 Claims, No Drawings

METHOD OF CONTROLLING THE GROWTH OF BACTERIA, FUNGI AND ALGAE USING MEMBERS OF THE CLASS OF OXAZOLIDINES

This is a division, of copending application Ser. No. 469,200, filed May 13, 1974.

BACKGROUND OF THE INVENTION

This invention relates to a method of controlling the growth of bacteria, fungi, algae and certan viruses. In a particular aspect this invention relates to a method of controlling the growth of bacteria, fingi, alage and viruses by applying thereto certain members of the class of oxazolidines.

Oxazolines have long been known in the art. They are readily prepared by reacting an amino alcohol with an aldehyde:

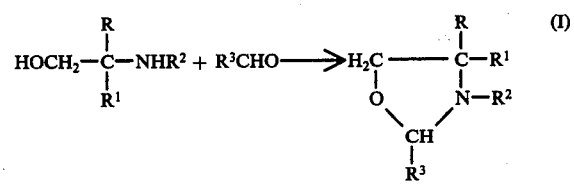

If the amino alcohol is a diol and 2 moles of aldehyde are used, the resulting oxazolidine is bicyclic, as described by M. Senkus, J. Am. Chem. Soc. 67, 1515–1519 (1945) and Wm. B. Johnston, U.S. Pat. No. 2,448,890, which are incorporated herein by reference thereto:

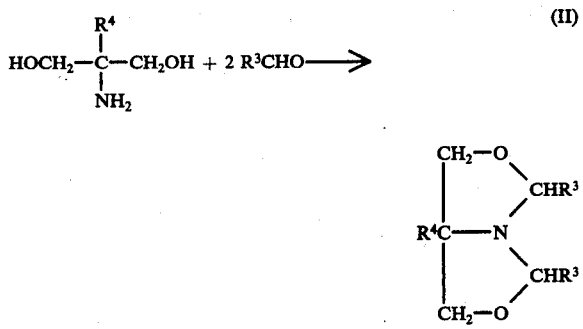

It is an object of this invention to provide a method of controlling the growth of micro-organisms and certain viruses.

It is another object of this invention to control the growth of bacteria, fungi, algae and viruses by applying thereto certain members of the class of oxazolidines.

It is yet another object of this invention to provide novel oxazolidines.

Other objects of this invention will be apparent to those skilled in the art from the disclosure herein.

It has been discovered that the growth of many micro-organisms, i.e., bacteria, fungi, algae, and certain viruses is controlled by applying to these organisms an oxazolidine corresponding to formula I wherein R and $R^1$ can be hydrogen or alkyl of 1 or 2 carbons and can be the same or different; $R^2$ can be hydrogen or alkyl of from 1 to 3 carbon atoms, or the group represented by the formula:

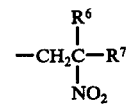

where $R^6$ can be hydrogen, methyl, or ethyl and $R^7$ can be methyl, hydroxymethyl, ethyl or the group

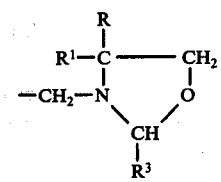

or a bicyclic oxazolidine corresponding to formula II, where $R^4$ can be hydrogen, alkyl of 1 or 2 carbon atoms, hydroxyalkyl, e.g. hydroxymethyl, or acyloxymethyl corresponding to the formula $-CH_2OOCR^5$ where $R^5$ is an alkyl group of 1 or 2 carbon atoms $R^3$ is hydrogen, alkyl or from 1 to 3 carbon atoms, hydroxyphenyl. The invention also contemplates a class of oxazolidine compounds believed to be novel wherein $R^2$ of formula I is nitroalkyl, viz., 2-nitro-2-methyl-1-propyl, 2-nitro-1-butyl or 2-nitro-1-propyl, or 2-nitro-1-ethyl, or nitrohydroxy alkyl.

DETAILED DESCRIPTION

Some of the oxazolidines used in the practice of this invention are commercially available and the usual commercial materials are suitable. 4,4-Dimethyl-1,3-oxazolidine is generally known as Oxazolidine A and this designation is employed in the examples. The bicyclic oxazolidine wherein $R^4$ is ethyl is known as Oxazolidine E and this designation is used in the examples. The bicyclic oxazolidine wherein $R^4$ is hydroxymethyl is known as Oxazolidine T and this designation is used in the examples. Other oxazolidines, i.e., esters thereof and those made from aldehydes other than formaldehyde, can be made by the method of M. Senkus or Wm. B. Johnston or J. A. Frump, U.S. Pat. No. 3,738,992.

When $R^2$ is nitroalkyl, the oxazolidines are prepared by condensing an oxazolidine represented by formula I with a nitroalkane and an aldehyde (or with a corresponding nitralcohol), [vis.,] to produce compounds corresponding to the formula

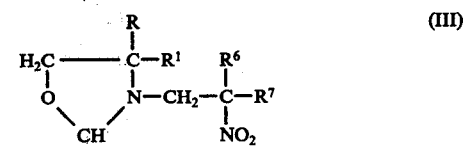

where $R^6$ is hydrogen, methyl, or ethyl, and $R^7$ is methyl, ethyl or hydroxymethyl, or $R^7$ can be

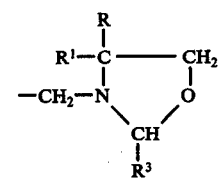

wherein R, R¹ and R³ have the same meaning as hereinbefore defined.

Most of these oxazolidines are water-soluble and are conveniently applied to the environment inhabited by micro-organism as a water solution. They are particularly effective in aqueous systems such as starch adhesives and solutions, drilling muds for the petroleum industry and in water-dilutable cutting oils based on petroleum hydrocarbons. A concentration of about 10–1000 μg/ml is required, but generally about 100–500 μg/ml is sufficient for all but the heaviest infestations.

These oxazolidines, especially the esters, are also soluble in, e.g., alcohols, ketones and most other organic solvents, including hydrocarbons. Solutions of the water-insoluble oxazolidines in such solvents can be used in substantially non-aqueous or 2-phase systems when desired.

A class of oxazolidines preferred for the practice of this invention is that wherein R² is represented by the formula

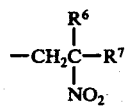

wherein R⁶ and R⁷ have the same meanings as hereinbefore defined. These compounds, which are believed to be novel, are prepared by mixing one mole of a nitroalkane, e.g. nitroethane, 1-nitropropane or 2-nitropropane, with 1 or 2 moles of formaldehyde, then adding 1 or 2 moles of an oxazolidine corresponding to formula I wherein R² is hydrogen preferably at an elevated temperature, e.g. 60°–70° C. The crude product is easily recovered by separating the water of solvent introduced with the formaldehyde (and also the water of reaction) by distillation.

The formaldehyde is preferably supplied as the 37% aqueous solution, but more concentrated solutions can also be used as is readily apparent. The formaldehyde can also be supplied as a solution in a lower alkanol, which solutions are commercially available, or as paraformaldehyde.

It is well-known in the art that nitroalkanes condense with one mole of formaldehyde to form a nitroalcohol, or with two moles of formaldehyde to form a nitroalkanediol. It is believed that this reaction proceeds prior to or during the reaction with the oxazolidine. Hence nitrohydroxy compounds, which are commercially available, can be substituted for the nitroalkane and formaldehyde in the process and are regarded as the practical equivalents thereof.

The invention will be better understood by reference to the following examples. It is understood, however, that the examples are intended only for the purpose of illustration and it is not intended that the invention be limited thereby.

EXAMPLE 1

Oxazolidine A (4,4-dimethyl-1,3oxazolidine) was tested by the Streak Plate Method, which is known in the art. The oxazolidine was incorporated into several portions of an agar medium at several known concentrations and the mixtures were placed in Petri dishes. Then streaks of test organisms were applied to the surface of the medium and the dishes were incubated under growth-promoting conditions, then examined for growth of organisms. The results are reported as a range, the lower figure signifying a concentration that allows growth and the upper being a concentration that inhibits growth.

The results are as follows:

| BACTERIA | Inhibiting concentration |
|---|---|
| Staphylococcus aureus | 100–500 μg/ml |
| Streptococcus fecalis | 100–500 |
| Streptococcus hemolyticus | 100–500 |
| Escherichia coli | 100–500 |
| Pasteurella pseudotuberculosis | 50–100 |
| Pseudomonas aeruginosa | 100–500 |
| Shigella dysenteriae | 100–500 |
| Mycobacterium tuberculosis | 100–500 |
| FUNGI | |
| A. niger | 500–1000 μg/ml |
| Candida albicans | 1000 |
| Penicillium species | 500–1000 |
| A. fumigatus | 100–500 |
| ALGAE | |
| Six species of green and blue-green | 19.5–156 μg/ml |
| VIRUS | |
| Newcastle's strain | 100–1000 μg/ml |
| Boney-1 strain | 100–1000 |

EXAMPLE 2

A cutting oil emulsion was prepared according to the following formula:

| Light mineral oil | 20 parts |
|---|---|
| Water | 74 |
| Oxazolidine A | 3 |
| Mixed C₁₈ Fatty Acids | 3 |
| | 100 |

The emulsion was then tested by the streak test method. The results were reported as the range of concentration of Oxazolidine A, between which growth is allowed and complete inhibition is achieved, for the organisms listed.

| BACTERIA | Inhibiting Concentration |
|---|---|
| Staphylococcus aureus | 100–500 μg/ml |
| Streptococcus fecalis | 100–500 |
| Streptococcus hemolyticus | 100–500 |
| Escherichia coli | 100–500 |
| Pasteurella pseudotuberculosis | 50–100 |
| Pseudomonas aeruginosa | 100–500 |
| Shigella dysenteriae | 10– 50 |
| Mycobacterium tuberculosis | 100–500 |
| FUNGI | |
| A. niger | 500–1000 μg/ml |
| Candida Albicans | 1000 |
| Penicillium species | 100–500 |
| A. fumigatus | 100–500 |

EXAMPLE 3

The object of the following experiment was to determine the concentration of Oxazolidine A required to prevent attack by soil organisms on a starch-based drilling mud.

A starch solution, simulating a starch-based drilling mud, was prepared by dispersing 100 g of starch in 150 g of deionized water, then diluting with 2000 g of deionized water. Aliquots of 200 g each of this solution were then delivered to 4 oz. jars.

A suspension of soil organisms was prepared by extracting 5 g of ordinary soil with 100 ml of water. To the starch solution in each of the 4 oz. jars was added 1 ml of the suspension of soil micro-organisms. The pH was adjusted to 7 and to each of 3 jars there was added sufficient Oxazolidine A to provide a concentration of 0.1%, 0.2% and 0.3%, respectively. The jars were then incubated at 37° C for 96 hours.

After the incubation period, sterile agar plates were inoculated with supernatant liquid from the jars. The plates were then incubated for another 24 hours and results were recorded as growth or no growth. None of the samples treated with Oxazolidine A showed any growth. A control sample without bactericide showed growth.

EXAMPLE 4

The experiment of Example 3 was repeated in all essential details except that one group of samples was adjusted to pH 5 and another to pH 9. No growth was observed in those treated with Oxazolidine A but growth did occur in the controls without bactericide.

EXAMPLE 5

The experiments of Examples 3 and 4 were repeated in all essential details except that 1-aza-5-ethyl-3,7-dioxabicyclo-[3.3.0]-octane (Oxazolidine E) was substituted for Oxazolidine A. At 0.1% concentration, growth occurred at all pH levels. At 0.2% and 0.3% concentrations, no growth occurred regardless of pH.

The experiment of Example 1 was repeated in all essential details except that Oxazolidine E was substituted for A, and algae and viruses were omitted. The compound was effective against the bacteria and two fungi at a concentration of 1000 μg/ml or less as shown in Table 1.

EXAMPLE 6

The experiment of Example 5 was repeated in all essential details except that 1-aza-5-hydroxymethyl-3,7-dioxabicyclo-[3.3.0]-octane (Oxazolidine T) was substituted for Oxazolidine E. Growth occurred at 0.1% concentration at all pH levels but no growth occurred at 0.2% concentration at any pH. Anomalously, at 0.3%, growth occurred at pH 5, but not at pH 7 or 9. The finding at pH 5 is believed to be unreliable but was not checked.

The experiment of Example 1 was repeated in all essential details except that Oxazolidine T was substituted for A and algae and viruses were omitted. The compound was effective against the bacteria and two fungi at a concentration of 1000 μg/ml or less as shown in Table 1.

EXAMPLE 7

The experiment of Example 1 is repeated in all essential details except that 1,3-oxazolidine is substituted for 4,4-dimethyl-1,3-oxazolidine (Oxazolidine A). Inhibition of bacteria, fungi, algae and the virus strains is obtained at concentrations of 10 – 1000 μg/ml.

EXAMPLE 8

N-Methyl-2-amino-2-methyl-1-propanol, 51.5 g (0.45 mole) and 37% formaldehyde 40.5 g (0.46 mole) were mixed and allowed to stand overnight at room temperature. The mixture was then distilled and the fraction obtained at 130° was taken as the product. There was obtained 3,4,4-trimethyl-1,3-oxazolidine. It was effective against bacteria and two fungi at a concentration of 500 μg/ml or less shown in Table 1.

EXAMPLE 9 – 12

The experiment of Example 1 was repeated in all essential details using bacteria and fungi except that each of the following oxazolidines was tested in place of Oxazolidine A:

| | |
|---|---|
| Example 9. | 4,4-Dimethyl-2-(2-hydroxyphenyl)-1,3-oxazolidine |
| Example 10. | Propionic acid ester of Oxazolidine T |
| Example 11. | 4-Ethyl-1,3-oxazolidine |
| Example 12. | 1-Aza-5-hydroxymethyl-2,8-dimethyl-3,7-dioxabicyclo[3.3.0]-octane* |

*Obtained by reacting tris(hydroxymethyl)aminomethane with acetaldehyde.

The results obtained were as follows:

TABLE I

| | GROWTH INHIBITING CONCENTRATION | | | | | | | | | | |
|---|---|---|---|---|---|---|---|---|---|---|---|
| EXAMPLE NO. | 5 | 6 | 8 | 9 | 10 | 11 | 12 | 13 | 14 | 15 | 16 | 18 |
| BACTERIA | | | | | | | | | | | |
| *Staphylococcus aureus* | D | D | C | D | C | C | D | C | B | B | B | B |
| *Streptococcus fecalis* | C | D | C | E | C | C | C | C | B | B | B | C |
| *Streptococcus hemolyticus* | D | D | D | E | C | C | D | C | B | B | B | B |
| *Escherichia coli* | E | D | D | C | E | C | D | C | B | B | B | B |
| *Pasteurella pseudotuberculosis* | B | D | C | C | C | C | C | B | A | AA | A | A |
| *Pseudomonas aeruginosa* | E | D | D | D | E | C | D | C | B | D | B | B |
| *Shigella dysenteriae* | D | D | C | D | C | C | D | C | B | D | B | B |
| *Mycobacterium tuberculosis* | D | D | D | — | C | C | C | C | A | — | A | B |
| FUNGI | | | | | | | | | | | |
| *A. Niger* | E | E | D | B | E | D | E | C | A | A | A | B |
| *Candida albicans* | E | E | B | B | E | E | E | D | A | A | A | B |
| *Penicillium species* | D | B | D | B | E | C | E | C | A | A | A | A |
| *A fumigatus* | D | B | D | B | E | C | E | C | A | A | A | A |

AA = 1–10 μg/ml
A = 10–50 μg/ml
B = 50–100 μg/ml
C = 100–500 μg/ml
D = 500–1000 μg/ml
E = >1000 μg/ml

EXAMPLE 13

2-Nitropropane 89 g (1 mole) and 37% formaldehyde 88 g (1 mole) were mixed together and heated to 65° C. There was then added dropwise Oxazolidine A 101 g (1 mole) and after the addition was complete, heating of the reaction mixture at 60°–70° C was continued for 2 hours. Water was then removed by distillation at about 8–12 mm Hg pressure. There was obtained N-(2-methyl-2-nitropropyl)-4,4-dimethyl-1,3-oxazolidine. It analyzed carbon 53.65% (calc. 53.47), hydrogen 9.07% (calc. 8.98) and nitrogen 13.47% (calc. 13.87). The compound was effective against bacteria and fungi at a concentration of 500 μg/ml or less as shown in Table 1.

EXAMPLE 14

The experiment of Example 13 was repeated in all essential details except that 1-nitropropane was substituted for 2-nitropropane. There was obtained N-(2-nitrobutyl)-4,4-dimethyl-1,3-oxazolidine. It was effective against bacteria and fungi at a concentration of 100 μg/ml or less as shown in Table 1.

EXAMPLE 15

The experiment of Example 14 was repeated in all essential details except that 2 moles of formaldehyde were substituted for 1 mole. There was obtained N-3-(2-ethyl-2-nitro-1-propanol)-4,4-dimethyl-1,3-oxazolidine. The compound was effective against bacteria and fungi at a concentration of 100 μg/ml or less as shown in Table 1.

EXAMPLE 16

1-Nitropropane, 89 g (1 mole) 37% formaldehyde, 162 g (2 moles), were mixed and heated to 60°–70° C. Oxazolidine A, 253 g (2 moles) was added dropwise and after addition was complete, heating was continued for 2 hours. The solution was then distilled at reduced pressure to remove water. There was obtained 250 g of residue having a neutral equivalent of 204.1. It was determined to be 2-nitro-2-ethyl-1,3-bis(4,4-dimethyl-1,3-oxazolidinyl)-propane. It was effective against both bacteria and fungi at 100 μg/ml or less as shown in Table 1.

EXAMPLE 17

The experiment of Example 16 is repeated in all essential details except that nitroethane, (1 mole), is substituted for 1-nitropropane. There is obtained 2-nitro-2-methyl-1,3-bis(4,4-dimethyl-1,3-oxazolidinyl)-propane. It is effective against both bacteria and fungi.

EXAMPLE 18

Nitroethane 102 g (1.36 moles) was mixed with 37% formaldehyde 211 g (2.6 moles) and 1200 g of water. The temperature was adjusted to 25°–35° C. and Oxazolidine A 210 g (2.08 moles) was added dropwise. The mixture was then heated at about 60° C for about 3 hours. The mixture was allowed to cool whereupon crystals separated. They were recovered by filtration, and washed with cold isopropyl alcohol. There was obtained 2-nitro-2-methyl-1,3-bis-(4,4-dimethyl-1,3-oxazolidinyl)-propane. It had a neutralization equivalent of 160.9 (calc. 150.5) and a melting point of 107.6°. It was effective against bacteria and fungi as shown in Table I.

I claim:

1. A method of controlling the growth of bacteria, fungi, green and blue green algae and Newcastle's and Boney viruses by applying to these organisms or to the environment inhabited by them growth-inhibiting amounts of 10 μg/ml to 1000 μg/ml of an oxazolidine represented by the formula:

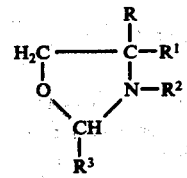

where R and $R^1$ are hydrogen or alkyl of 1 or 2 carbon atoms and can be the same or different; $R^2$ is alkyl of from 1 to 3 carbon atoms, and $R^3$ is hydroxyphenyl.

2. A method of controlling the growth of bacteria, fungi, green and blue green algae and Newcastle's and Boney viruses by applying to these organisms or to the environment inhabited by them growth-inhibiting amounts of 10 μg/ml to 1000 μg/ml of an oxazolidine represented by the formula

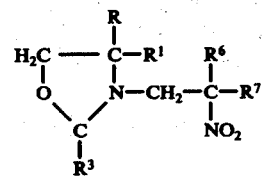

where R and $R^1$ are hydrogen or alkyl of 1 or 2 carbon atoms an can be the same or different; $R^3$ is hydrogen, alkyl of from 1 to 3 carbon atoms or hydroxyphenyl; $R^6$ is hydrogen, methyl, or ethyl and $R^7$ is methyl, hydroxymethyl, or ethyl.

3. The method of claim 2 wherein $R^6$ is hydrogen and $R^7$ is ethyl.

4. The method of claim 2 wherein $R^6$ and $R^7$ are methyl.

5. The method of claim 2 wherein $R^6$ is hydrogen and $R^7$ is ethyl.

6. The method of claim 2 wherein $R^6$ is ethyl and $R^7$ is hydroxymethyl.

* * * * *

UNITED STATES PATENT AND TRADEMARK OFFICE
CERTIFICATE OF CORRECTION

PATENT NO. : 4,066,433
DATED : January 3, 1978
INVENTOR(S) : Jerry H. Hunsucker

It is certified that error appears in the above-identified patent and that said Letters Patent are hereby corrected as shown below:

Column 1, line 11, "certan" should read -- certain --

Column 1, line 13, "fingi" should read -- fungi --

Column 1, line 13, "alage" should read -- algae --

Column 2, line 24, after the comma insert -- or --

Column 2, line 49, "[vis.,]" should read -- [viz.,] --

Signed and Sealed this

Twenty-seventh Day of June 1978

[SEAL]

Attest:

RUTH C. MASON
*Attesting Officer*

DONALD W. BANNER
*Commissioner of Patents and Trademarks*